United States Patent [19]

Bagli et al.

[11] Patent Number: 4,542,140

[45] Date of Patent: Sep. 17, 1985

[54] PYRIDINYL SUBSTITUTED KETENEMERCAPTAL DERIVATIVES

[75] Inventors: Jehan Bagli, Kirkland; Tibor Bógri, Montreal; Bozidar Palameta, Dollard des Ormeaux; Luis E. Borella, Beaconsfield, all of Canada

[73] Assignee: American Home Products Corporation, New York, N.Y.

[21] Appl. No.: 543,712

[22] Filed: Oct. 20, 1983

[51] Int. Cl.[4] .................. A61K 31/44; C07D 213/32; C07D 213/62; C07D 401/12

[52] U.S. Cl. .................. 514/332; 514/335; 514/345; 514/346; 514/348; 514/350; 514/351; 514/354; 514/357; 546/261; 546/263; 546/264; 546/265; 546/291; 546/296; 546/298; 546/300; 546/315; 546/326; 546/330

[58] Field of Search ............ 546/330, 261, 264, 263, 546/300, 265, 326, 315, 291, 296, 298; 424/263

[56] References Cited

U.S. PATENT DOCUMENTS

| | | | |
|---|---|---|---|
| 2,600,380 | 1/1952 | Derek | 546/330 |
| 2,638,473 | 5/1953 | Derek | 546/330 |
| 3,136,689 | 6/1964 | Miller | 424/45 X |
| 3,404,161 | 10/1968 | Strobel et al. | 546/264 X |
| 3,590,068 | 6/1971 | Toepfl et al. | 544/85 X |
| 4,067,984 | 1/1978 | Durant et al. | 546/261 X |
| 4,238,405 | 12/1980 | Felix | 544/316 X |
| 4,282,231 | 8/1981 | Felix | 424/263 |

FOREIGN PATENT DOCUMENTS

| | | | |
|---|---|---|---|
| 242004 | 10/1960 | Australia | 546/264 |
| 1027141 | 2/1978 | Canada . | |
| 597446 | 1/1948 | United Kingdom . | |
| 1111446 | 4/1968 | United Kingdom . | |
| 1122750 | 8/1968 | United Kingdom . | |

OTHER PUBLICATIONS

Heinemann et al., Chem. Abstracts, vol. 100:68302p (1984).
Chem. Abstr., 58, 9076–9077, (1963) for R. Gompper and W. Toepfl, Chem. Ber., 95, 2861 (1962).
K. Kumar et al., J. Chem. Soc., Chem. Commun., (15), 592 (1976).
Chem. Abstr., 86, 189791y (1977) for K. Peseke, J. Prakt. Chem., 318, 939 (1976).

*Primary Examiner*—Donald G. Daus
*Assistant Examiner*—William A. Teoli, Jr.

[57] ABSTRACT

α-Cyanoacrylic acid lower alkyl esters, and their corresponding amides, characterized by having a heterocyclic containing mercapto radical as one β-substituent and an alkylthio, alkenylthio or a heterocyclic containing mercapto radical as another β-substituent are useful for treating ulcers and for suppressing gastric acid secretion.

13 Claims, No Drawings

PYRIDINYL SUBSTITUTED KETENEMERCAPTAL DERIVATIVES

RELATED APPLICATION

Related hereto are U.S. patent application Ser. No. 543,711 and U.S. patent application Ser. No. 543,713, filed on the same date as this application.

BACKGROUND OF THE INVENTION

This invention concerns heterocyclic substituted ketenemercaptal derivatives, processes for preparing the derivatives, novel pharmaceutical compositions, and methods for using the derivatives.

The ketenemercaptal derivatives of this invention belong to a broad generic group of compounds known as α-cyano-β,β-dimercaptoacrylic acid derivatives. The broad generic group has received a considerable amount of attention. Most of this attention has been directed to the use of the derivatives as intermediates for preparing other compounds or to investigations of their chemical properties. For example, see J. D. Kendall and H. D. Edwards, U.K. Patent Specification No. 597,446, Jan. 27, 1948; R. Gompper and W. Toepfl, Chem. Ber., 95, 2861 (1962); A. Kumar et al., J. Chem. Soc., Chem. Commun., (15), 592 (1976); Chem. Abstr., 86, 189791 y (1977) for K. Peseke, J. Prakt. Chem., 318, 939 (1976); and H. B. Tinker and A. J. Solodar, Canadian Pat. No. 1,027,141, Feb. 28, 1978.

Certain ketenemercaptal derivatives of this class also have been reported to possess biological activities of the types which find use in agriculture. See, for example, K. Knoevenagel and R. Himmelreich, U.K. Patent Specification No. 1,111,446, published Apr. 24, 1968; W. Toepfl and M. von Orelli, U.S. Pat. No. 3,590,068, June 29, 1971; and K. Dickore et al., U.K. Patent Specification No. 1,122,750, published Aug. 7, 1968.

The ketenemercaptal derivatives of the present invention are distinguished readily from previously reported ketenemercaptals by having a particular heterocycle incorporated into their structure and by their unique use as agents for treating ulcers, hyperchlorhydria and associated conditions in animals.

SUMMARY OF THE INVENTION

The compounds of this invention are represented by formula I

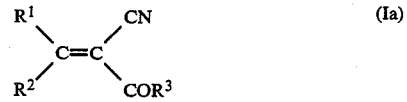
(I)

wherein $R^1$ is $S(CH_2)_m$—Het in which m is an integer from zero to three and Het is a heterocyclic radical selected from the group consisting of pyridinyl, (N-oxide)-pyridinyl, pyrazinyl, pyrimidinyl, pyridazinyl and thienyl, the heterocyclic radical being optionally substituted with a lower alkyl, lower alkoxy, halo, trifluoromethyl or $(CH_2)_nCOOQ$ wherein n is an integer from 0 to 2 and Q is lower alkyl; $R^2$ is lower alkylthio, lower alkenylthio or $S(CH_2)_m$—Het wherein m and Het are as defined herein; and $R^3$ is lower alkoxy or amino.

A preferred group of the compounds of this invention is represented by formula I wherein $R^1$ is $S(CH_2)_m$—Het wherein m is the integer zero or one and Het is as defined herein, $R^2$ is lower alkylthio or the same $S(CH_2)_m$—Het radical as selected for $R^1$, and $R^3$ is lower alkoxy or amino.

A more preferred group of the compounds of this invention is represented by formula I wherein $R^1$ is $S(CH_2)_m$—Het wherein m is the integer zero or one and Het is pyridinyl, (N-oxide)pyridinyl, pyrazinyl, pyrimidinyl, (lower alkyl)pyrimidinyl, pyridazinyl, thienyl, (lower alkyl)thienyl or halothienyl; $R^2$ is lower alkylthio and $R^3$ is lower alkoxy or amino.

A most preferred group of the compounds of this invention is represented by formula I wherein $R^1$ is $S(CH_2)_m$—Het wherein m is the integer one and Het is pyridinyl or thienyl, the thienyl being optionally substituted with a lower alkyl or halo; $R^2$ is lower alkylthio and $R^3$ is alkoxy or amino.

Also included within the scope of the invention are the therapeutically acceptable acid addition salts of the compounds of formula I which contain a basic nitrogen.

A method is provided for preventing or treating gastrointestinal ulcers in a mammal, or for preventing or decreasing the secretion or availability of excessive amounts of gastric acid in a mammal suffering from hyperchlorhydria.

The method comprises administering to the mammal in need thereof an effective amount of the compound of formula I or a therapeutically acceptable acid addition salt of the compounds containing a basic nitrogen.

A pharmaceutical composition in unit dosage form, for use according to the previous method, also is provided. The composition comprises the compound of formula I, or a corresponding therapeutically acceptable acid addition salt of the compounds containing a basic nitrogen, admixed with a pharmaceutically acceptable carrier.

The compounds of formula I are prepared by processes described hereinafter.

As noted previously, the compounds of this invention are α-cyano-β,β-dimercaptoacrylic acid derivatives. This type of derivative exists in two geometrical isomeric forms, namely E and Z, when the two β substituents are different. One of these isomeric forms can be represented by formula I and the other by formula Ia

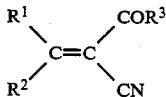
(Ia)

wherein $R^1$, $R^2$ and $R^3$ are as defined herein.

As a rule the compounds of this invention are obtained as a mixture of isomers. The percentages of the two isomers in a mixture is dependent partially on the physical and chemical environment of the compound. The isomeric forms can be separated, for example, by a careful choice of crystallization conditions. However, the use of the mixture, as well as an individual isomer, as the active agent for the invention is acceptable. Accordingly, the mixture of isomers, and the individual isomers, are included within the scope of this invention.

For convenience and brevity, the ketenemercaptal derivatives of this invention are represented by formula I throughout the application and the appended claims.

DETAILS OF THE INVENTION

The term "lower alkyl" as used herein means a straight chain alkyl radical containing from one to six carbon atoms or a branched chain alkyl radical containing three to six carbon atoms and includes methyl, ethyl, propyl, 1-methylethyl, butyl, 2-methylpentyl and 1,1-dimethylbutyl. Preferred lower alkyl radicals contain from one to three carbon atoms.

The term "lower alkenyl" as used herein means a straight chain alkenyl radical containing from two to six carbon atoms, or a branched chain alkenyl radical containing from four to six carbon atoms and includes, for example, ethenyl, 2-propenyl, 2-methyl-2-propenyl and 2-ethyl-3-butenyl. Preferred lower alkenyl radicals contain two to four carbon atoms.

The term "lower alkoxy" are used herein means a straight chain alkoxy radical containing from one to six carbon atoms, preferably one to three carbon atoms, or a branched chain alkoxy radical containing three to four carbon atoms, and includes methoxy, ethoxy, 1-methylethoxy, butoxy and hexanoxy.

The term "halo" as used herein means a halo radical and includes fluoro, chloro, bromo and iodo.

The term "organic proton acceptor" as used herein means the organic bases or amines for instance, triethylamine, pyridine, N-ethylmorpholine, 1,5-diazabicyclo[4.3.0]non-4-ene and the like.

The term "inorganic proton acceptor" as used herein means the inorganic bases, preferably the alkali metal hydrides, hydroxides and carbonates, or their corresponding lower alkoxides, for example, sodium hydride, potassium hydroxides, sodium carbonate, potassium carbonate and sodium ethoxide.

The term "proton acceptor" as used herein means a proton acceptor selected from an organic proton acceptor and an inorganic proton acceptor, as defined hereinabove.

The compounds of formula I containing one or more basic nitrogen atoms are capable of forming acid addition salts with therapeutically acceptable acids. The basic nitrogen-containing compounds of formula I are those in which the symbol Het is an optionally substituted pyridinyl, (N-oxide)pyridinyl, pyrazinyl, pyrimidinyl or pyridazinyl, as defined hereinabove. The acid addition salts are prepared by reacting the base form of the appropriate compound of formula I with one or more equivalents preferably with an excess of the appropriate acid in an organic solvent, for example, diethyl ether or an ethanol-diethyl ether mixture.

These salts, when administered to a mammal possess the same pharmacologic activities as the corresponding bases. For many purposes it is preferable to administer the salts rather than the base compounds. Suitable acids to form these salts include the common mineral acids, e.g. hydrohalic, sulfuric or phosphoric acid; the organic acids, e.g. maleic, citric or tartaric acid; and acids which are sparingly soluble in body fluids and which impart slow-release properties to their respective salts, e.g. pamoic or tannic acid or carboxymethyl cellulose. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

When a compound of formula I is administered to a mammal suffering from hyperchlorhydria and/or associated conditions for the purpose of preventing or decreasing the secretion of excessive amount of gastric acid or hydrochloric acid, or is used for the treatment of ulcers in mammals, it is used alone or in combination with pharmacologically acceptable carriers, the proportion of which is determined by the solubility and chemical nature of the compound, chosen route of administration and standard biological practice.

For example, the compound can be administered orally in solid form i.e. capsule or tablet, orally in liquid form, i.e. suspensions or solutions, or it can be injected parenterally. The preferred method of administration is to give it orally.

The tablet compositions can contain the compound of formula I in admixture with pharmaceutically acceptable excipients, for example, starch, milk, sugar etc. The tablets can be uncoated or they can be coated by known techniques so as to delay disintegration and adsorption in the gastrointestinal tract and thereby provide a sustained action over a longer period.

The aqueous suspensions for oral administration can contain the compound in admixture with one or more nontoxic pharmaceutical excipients known to be suitable in the manufacture of aqueous suspensions. Suitable excipients are, for example, methylcellulose, sodium alginate, gum acacia, lecithin, etc. The aqueous suspensions can also contain one or more preservatives, one or more coloring agents, one or more flavoring agents or one or more sweetening agents.

Non-aqueous suspensions for oral administration can be formulated by suspending the compound in a vegetable oil, for example, arachis oil, olive oil, sesame oil, or coconut oil, or in liquid paraffin, and the suspension may contain a thickening agent, for example, beeswax, hard paraffin or cetyl alcohol. These compositions can also contain a sweetening agent, flavoring agent or antioxidant.

For administration to a mammal by parenteral injection, it is preferred to use the compound in solution in a sterile aqueous vehicle, which may also contain other solutes such as buffers or preservatives, as well as sufficient quantities of pharmaceutically acceptable salts or of glucose to make the solution isotonic.

The dosage of the compound of formula I for combating or preventing hyperchlorhydria and/or associated conditions, or for the treatment of ulcers, in a mammal will vary with the form of administration and the particular compound chosen. Furthermore, it will vary with the particular host as well as the age, weight and condition of the host under treatment as well as with the nature and extent of the symptoms. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford effective results without causing any harmful or deleterious side effects. For example, an effective antiulcer amount, or an effective amount for preventing hyperchlorhydria and inhibiting hydrochloric acid secretion, of the compound usually ranges from about 1.0 mg to about 100 mg per kg of body weight per day in single or divided dose, although as aforementioned, variations will occur. However, a dosage level that is in the range from about 5.0 mg to about 50 mg per kg of body weight per day in single or divided dose is employed most desirably in order to achieve effective results.

Unit dosage forms such as capsules, tablets, syrups, suspensions and the like may contain from 10 mg to about 100 mg of the active agent of this invention with a pharmaceutical carrier.

The effectiveness of the compounds of formula I as agents for preventing hyperchlorhydria and inhibiting gastric acid secretion can be demonstrated readily in pharmacological tests. For example, the following test demonstrates their effectiveness in inhibiting spontaneous gastric acid secretion in cannulated rats.

Male albino Sprague Dawley rats (200-300 g), purchased from Canadian Breeding Laboratories, were employed. Two gastric cannulas were implanted surgically in each rat as described by L. E. Borella and F. Herr, Gastroenterology, 61, 345 (1971). The rats were used two to three weeks after the operation at a time when their food intake and weight gain were similar to the food intake and weight gain of unoperated litter mates. Before testing, the rats were deprived of food for 18 hours, but they had available a solution of 0.2% sodium chloride in 5% glucose for drinking ad libitum. Prior to each experiment, the plugs of the stomach cannulas of each rat were removed and the debris present in the stomach was flushed out with tepid saline passed through the cannulas. Thereafter, the lumen of the stomach was continuously perfused with saline introduced into the stomach through the forestomach cannula at a rate of 0.8-1.2 ml/min. The stomach perfusate flowing out of the antrum cannula was collected in 60 minutes intervals and the total acid in each collection was titrated with 0.05N sodium hydroxide employing phenol red as an indicator. After a period of acclimatization of about 60 to 90 minutes, the acid output values were recorded. On the basis of the hourly acid output, the rats were divided into equal groups so that the average acid output of all groups was similar. Saline (vehicle) or saline suspensions or solutions of the test compounds were administered intragastrically (i.g.) through the forestomach cannula, after having closed the antral cannula. During the one hour absorption period, the stomachs of the rats were not perfused. After the absorption period, perfusion of the stomachs was resumed, and the perfusates were collected hourly for three hours. The average post-treatment hourly acid outputs of the test compound groups were compared to that of the saline group and the percent inhibition of acid output was calculated. Multiple statistical comparisons between groups was done using Dunnet's t test, C. W. Dunnet, Journal of American Statistical Association, 50, 1096 (1955).

The following table shows the results obtained when compounds of formula I, listed therein, were evaluated in the preceding test.

by assessing their effects on gastric lesions induced in rats by absolute alcohol according to the method of A. Robert et al., Gastroenterology, 77, 433 (1979).

More explicitly exemplified, the beneficial effects were evaluated as follows: food was withheld from male albino rats (180-220 g, Sprague-Dawley, Canadian Breeding Laboratories) for 18 to 19 hours, but water was freely available. Test compounds were administered intragastrically (i.g.) by stomach gavage, 30 minutes before absolute ethanol. The absolute ethanol (one milliliter) also was administered by gavage. One hour after the alcohol treatment, the rats were killed and their stomachs removed for observation. Clotted blood was removed from the surface of the mucosa, and the macroscopic lesions counted. The average scores of the treatment groups were compared individually to that of the control group and percent inhibitions of lesion formation calculated. The data was analyzed statistically according to Dunnett's t test for multiple comparisons between groups.

The results obtained when 2-cyano-3-(methylthio)-3-[[3-pyridinyl)-methyl]thio]-2-propenoic acid methyl ester, described in example 1, was tested according to the previous method is as follows.

| Treatment | Dose (mg/kg, i.g.) | No. of Animals | Gastric Ulcers Formed Score | |
|---|---|---|---|---|
| | | | (mean ± S.E.) | % Inhibition |
| Vehicle | — | 18 | 17 ± 2 | |
| Test Compound | 10 | 9 | 0 | 100 |
| | 5 | 16 | 6.7 ± 2.2 | 61 |

PROCESS

The compounds of formula I wherein $R^1$, $R^2$ and $R^3$ are as defined herein can be prepared by a process comprising:

(a) reacting a compound of formula II

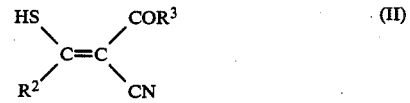

wherein $R^2$ is lower alkylthio or lower alkenylthio, and $R^3$ is lower alkoxy or amino with an organohalide of formula Het—$(CH_2)_m$—X wherein Het and m are as

| Compound of Formula I | | | | Example in Which Compound is Prepared | Percent Inhibition of Acid Output (25 mg/kg/i.g., unless noted otherwise) |
|---|---|---|---|---|---|
| m | Het | $R^2$ | $R^3$ | | |
| 1 | 3-pyridinyl | $SCH_3$ | $OCH_3$ | 1 | 85 |
| 1 | (N—oxide)-3-pyridinyl | $SCH_3$ | $OCH_3$ | 2 | 60 |
| 1 | 3-pyridinyl | 3-pyridinyl-methyl thio | $OCH_3$ | 1 | 38 |
| 0 | 3-methylpyridazinyl | $SCH_3$ | $OCH_3$ | 3 | 90[1,2] |
| 1 | 3-pyrazinyl | $SCH_3$ | $OCH_3$ | 4 | 88[1,2] |
| 1 | 3-pyridinyl | $SCH_3$ | $NH_2$ | 12 | 27 |
| 1 | 4-pyridinyl | $SCH_3$ | $NH_2$ | 13 | 59[1] |

[1] 50 mg/kg/i.g.
[2] Tested as hydrochloric acid addition salt

The beneficial effect of the compounds of formula I on gastrointestinal ulcer formation can be demonstrated defined herein and X is bromo, chloro or iodo in the presence of a proton acceptor to obtain the corresponding compound of formula I wherein $R^1$ and $R^3$ are as defined herein, and $R^2$ is lower alkylthio or lower alkenylthio; or (b) reacting a compound of formula III

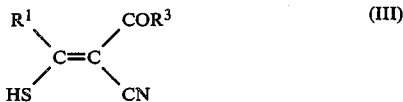

wherein $R^1$ and $R^3$ are as defined herein with an organohalide of formula Het—$(CH_2)_m$—X wherein Het and m are as defined herein and X is bromo, chloro or iodo in the presence of a proton acceptor to obtain the corresponding compound of formula I wherein $R^1$ and $R^2$ each is the same or different $S(CH_2)_m$—Het wherein m and Het are as defined herein and $R^3$ is lower alkoxy or amino; or (c) disproportionating a compound of formula I wherein $R^1$, $R^2$ and $R^3$ are as defined herein, provided that $R^1$ and $R^2$ are different, to obtain the corresponding compound of formula I wherein $R^1$ and $R^3$ are as defined herein and $R^2$ is the same $S(CH_2)_m$—Het radical as that for $R^1$; and (d) if required, transforming the compound of formula I having a basic nitrogen atom into a corresponding, therapeutically acceptable acid addition salt.

The starting materials of formula II are either known or can be prepared by known methods. For example, the starting materials of formula II, 2-cyano-3-mercapto-3-(methylthio)-2-propenoic acid methyl ester and 2-cyano-3-mercapto-3-(methylthio)-2-propenamide, and a general method for making the compounds of formula II are described by R. Gompper and W. Toepfl, Chem. Ber., 95, 2861 (1962).

The organohalides of formula Het—$(CH_2)_m$—X are known, many of them being available commercially. They also can be prepared by conventional methods; for example, see T.-Y. Shen and C. P. Dorn, U.S. Pat. No. 3,558,640, issued Jan. 26, 1971.

The starting materials of formula III are prepared by reacting approximately one molar equivalent of the aforementioned organohalide with a 2-cyano-bis(3-mercapto)-2-propenoic acid lower alkyl ester or a 2-cyano-bis(3-mercapto)-2-propenamide, according to the method of R. Gompper and W. Toepfl, cited above.

With reference to paragraph (a) of the above statement itemizing the process for preparing compounds of formula I, the compounds of formula I wherein $R^1$ and $R^3$ are as defined herein and $R^2$ is lower alkylthio or lower alkenylthio can be prepared by reacting the corresponding compound of formula II wherein $R^2$ is lower alkylthio or lower alkenylthio and $R^3$ is lower alkoxy or amino with 1.0 to 1.5 molar equivalents of the appropriate organic halide of formula Het—$(CH_2)_m$—X wherein Het, m and X are as defined herein in the presence of a proton acceptor in a suitable inert organic solvent. Suitable inert organic solvents for this reaction include dimethylformamide, acetonitrile, tetrahydrofuran, acetone and toluene. The reaction is performed in the presence of either an inorganic or organic acceptor. On a molar basis, the amount of the proton acceptor generally used is at least equivalent to the amount of the compound of formula II employed, preferably one to one and a half molar equivalents. Suitable proton acceptors include sodium carbonate, potassium carbonate and triethylamine. Preferred conditions include the use of an inorganic proton acceptor, for example, sodium carbonate or potassium carbonate, and the use of a water miscible organic solvent, for example, dimethylformamide or acetonitrile, optionally diluted with water. Although the optimum temperature and reaction time will vary depending on the reactants employed, the reaction usually is performed at 0° to 100° C., or at the boiling point of the reaction mixture, for 10 minutes to 48 hours, preferably at 10° to 35° C. for 30 minutes to 24 hours.

When performing the latter reaction, stringent conditions, such as prolonged reaction times or elevated temperatures, should be avoided because such conditions lead to the formation of byproducts, namely compounds of formula I wherein $R^1$ and $R^2$ are identical radicals. In this instance, the byproducts are the results of the disproportionation of the desired product and their formation can be minimized by monitoring the progress of the reaction to determine optimum reaction time by thin layer chromatography on aliquots of the reaction mixture. On the other hand, when it is desired to prepare compounds of formula I wherein $R^1$ and $R^2$ are identical radicals, the more stringent conditions can be used to advantage. This point will be discussed hereinafter.

With reference to paragraph (b) of the above statement itemizing the process for preparing compounds of formula I, the compound of formula I wherein $R^1$ and $R^3$ are as defined herein and $R^2$ is $S(CH_2)_m$—Het wherein m and Het are as defined herein are prepared by reacting the compound of formula III wherein $R^1$ and $R^3$ are as defined herein with the organohalide of formula Het—$(CH_2)_m$—X wherein Het, m and X are as defined herein in the presence of an organic acceptor to obtain the desired corresponding compound of formula I. Suitable proton acceptors, organic solvents, reactions times and temperatures for performing this reaction are the same as those described above for the process of paragraph (a), i.e. the reaction of a compound of formula II with an organohalide.

In general, the compounds of formula I are stable, especially in their crystalline state. However, in the presence of a source of free mercapto radicals of a species different from the species derived from a particular mercapto substituent of the compound of formula I, the compound can undergo disproportionation. Compounds of formula I wherein $R^1$ or $R^2$ is $S(CH_2)_m$—Het wherein m is the integer one are more prone to undergo disproportionation. Conditions which promote disproportionation of the compounds are the exposure of the amorphous form of the compound, or a solution of the compound, to elevated temperatures, to prolonged storage time and to light. Hence, such conditions ordinarily should be avoided or minimized.

However, the property of the compounds of formula I to undergo disproportionation can be used to advantage to prepare certain compounds of formula I. More specifically, with reference to paragraph (c) of the above statement itemizing the process for preparing compounds of formula I, compounds of formula I wherein $R^1$ and $R^2$ each is the same $S(CH_2)_m$—Het radical are obtained by disproportionation of a corresponding compound of formula I wherein $R^1$ and $R^3$ are as defined herein and $R^2$ is lower alkylthio or lower alkenylthio. More specifically, and by way of example, the disproportion can be effected by allowing the compound of formula I wherein $R^1$ and $R^3$ are as defined herein and $R^2$ is lower alkylthio or lower alkenylthio, in its amorphorus state, to stand in the presence of light for an extended period of two to four weeks at 20° to 60° C., or by subjecting the compound to the action of an inorganic proton acceptor in a media of a water miscible solvent such as dimethylformamide or acetonitrile at temperatures ranging from 20° to 100° C. for four to 48 hours.

The following examples illustrate further this invention.

EXAMPLE 1

2-Cyano-3-(methylthio)-3-[[(3-pyridinyl)methyl]thio]-2-propenoic Acid Methyl Ester (I; $R^1$=(3-pyridinyl)methylthio, $R^2$=CH$_3$S and $R^3$=OCH$_3$)

2-Cyano-3-mercapto-3-(methylthio)-2-propenoic acid methyl ester (7.6 g), described by R. Gompper and W. Toepfl, Chem. Ber., 95, 2861 (1962), and the organohalide, 3-(chloromethyl)pyridine hydrochloride (6.6 g), was suspended in acetonitrile (20 mL). A solution of potassium carbonate (8.2 g) in water (20 mL) was added to the suspension and the resulting mixture was stirred vigorously for 7 hrs at 25° C. Thereafter, the mixture was diluted with water and extracted with chloroform. The extract was dried (Na$_2$SO$_4$) and concentrated to dryness. The residue was subjected to chromatography on silica gel using dichloromethane-ethyl acetate (7:3, v/v) as the eluant. The pure fractions were pooled and crystallized from diethyl ether to yield the title compound; mp 60°–62° C.; NMR (CDCl$_3$) δ 2.5 (s, 3H), 3.8 (s, 3H), 4.37 (s, 2H), 7.7 (m, 4H); IR (CHCl$_3$) 2210, 1710 cm$^{-1}$; UV λ max(MeOH) 332 nm (ε 12,700), 264 (5,000) with a shoulder at 269 nm; Anal. Calcd. for C$_{12}$H$_{12}$N$_2$O$_2$S$_2$: C, 51.41% H, 4.32% N, 10.00%; Found: C, 51.17% H, 4.24% N, 9.87%.

The corresponding hydrochloric acid addition salt, prepared by bubbling dry hydrogen chloride into a solution of the title compound in dichloromethane, had mp 172°–174° C. (after recrystallization from ethanol) and NMR (DMSO-d$_6$) δ 2.6 & 2.7 (2s, 3H), 3.75 (s, 3H), 4.55 & 4.62 (s, 2H), 6.3 (broad, 1H), 8.4 (m, 4H).

Amorphous samples of the title compound, such as obtained from the above chromatogram, undergo disproportionation on standing. For example, after standing for two weeks unprotected from light, an amorphous sample (5.0 g) was subjected to chromatography on silica gel using chloroform-methanol (98:2, v/v) as the eluant to give 0.6 g of the known compound 2-cyano-3,3-bis(methylthio)-2-propenoic acid methyl ester, 3.5 g of the title compound, and 0.8 g of 2-cyano-3,3-bis[[(3-pyridinyl)methyl]thio]-2-propenoic acid methyl ester. The latter compound had mp 97°–99° C. (after recrystallization from ethanol); NMR (CDCl$_3$) δ 3.83 (s, 3H), 4.2 (s, 2H), 4.35 (s, 2H), 7.4 (m, 4H), 8.55 (m, 4H); IR (CHCl$_3$) 2210, 1701 cm$^{-1}$; UV λ max (MeOH) 331 nm (ε 13,010), 264 (8,580); Anal. Calcd. for C$_{17}$H$_{15}$N$_3$O$_2$S$_2$: C, 57.12% H, 4.23% N, 11.75%; Found: C, 57.42% H, 4.22% N, 11.75%.

The latter compound also is obtained by subjecting the title compound to the action of potassium carbonate in a medium of aqueous acetonitrile for 24 to 48 hrs at 20° to 25° C.

EXAMPLE 2

2-Cyano-3-(methylthio)-3-[[(3-pyridinyl)methyl]thio]-2-propenoic Acid Methyl Ester N-oxide (I; $R^1$=[(N-Oxide)-3-pyridinyl]methylthio, $R^2$=CH$_3$S and $R^3$=OCH$_3$)

A solution of potassium hydrogen carbonate (7.0 g) in water (70 mL) was added dropwise to an ice-cooled (ca. 0° to 2° C.), stirred suspension of 2-cyano-3-mercapto-3-(methylthio)-2-propenoic acid methyl ester (18.5 g) and the organohalide, 3-(chloromethyl)pyridine N-oxide (10 g) described by F. Gadient et al., Helv. Chim. Acta, 45, 1860 (1962), in acetonitrile (70 mL). While the reaction mixture was maintained at 0° to 2° C., an additional quantity (5.0 g) of the propenoic acid methyl ester derivative was added, followed by the dropwise addition of a solution of sodium hydrogen carbonate (5.0 g) in water (24 ml). The reaction mixture was first diluted with glacial acetic acid (3 ml), then diluted with water, and extracted with chloroform. The aqueous phase was mixed with acetic acid (5 ml) and extracted with chloroform. The combined chloroform extracts were evaporated to dryness. The residue was subjected to chromatography on silica gel using dichloromethane-methanol-acetic acid (8:1:1, v/v/v) as eluant. The pure fractions were pooled to give 10 g of an amorphous white powder which after crystallization from methanol gave the title compound; mp 108°–110° C.; NMR (CDCl$_3$) δ 2.5 (s, 3H), 3.9 (s, 3H), 4.3 (s, 2H), 7.3 and 8.3 (m, 4H); IR (CHCl$_3$) 2210, 1710, 1270 cm$^{-1}$; UV λ max (MeOH) 331 nm (ε 12,200), 268 (13,700); Anal. Calcd. for C$_{12}$H$_{12}$N$_2$O$_3$S$_2$: C, 48.63% H, 4.08% N, 9.45%; Found: C, 48.64% H, 4.06% N, 9.30%.

The corresponding hydrochloric acid addition salt, prepared by bubbling dry hydrogen chloride into a solution of the title compound in dichloromethane, had mp 128°–130° C. (after crystallization from ethanol); NMR (DMSO—d$_6$) δ 2.6 & 2.7 (2s, 3H), 3.75 (s, 3H), 4.45 & 4.5 (s, 2H), 8.1 (m, 4H).

By following the procedure of example 1 or 2 and using an equivalent amount of the appropriate organohalide other compounds of formula I in which $R^3$ is methoxy are obtained. Examples of the latter compounds are listed in Table I together with the organohalide used for the preparation of the compound.

TABLE I

| Example | Organohalide | Product: |
|---|---|---|
| 3 | 4-chloro-3-methylpyridazine | 2-cyano-3-[(3-methyl-4-pyridazinyl)thio]-3-(methylthio)-2-propenoic acid methyl ester; the corresponding hydrochloric acid addition salt had mp 160–162° C. (dec); NMR (DMSO-d$_6$) δ 2.45 (s, 3H), 2.7 (s, 3H), 3.8 (s, 3H), 7.7 & 9.07 (d, J = 5.5 Hz, 2H), 10 (broad, 1H); IR (white mineral oil) 2240, 2210, 1980, 1710 cm$^{-1}$; UV λ max (MeOH) 329 nm (ε 14,100), 209 (6,640), 211 (6,710); Anal Calcd for C$_{11}$H$_{11}$N$_3$O$_2$S$_2$.HCl: C, 41.51% H, 3.81% N, 13.22%; Found: C, 41.49% H, 3.77% N, 13.25%. |
| 4 | 2-(chloromethyl)-pyrazine | 2-cyano-3-(methylthio)-3-[[(3-pyrazinyl)methyl]thio]-2-propenoic acid methyl ester; NMR (CDCl$_3$) δ 2.53 & 2.7 (2s, 3H), 3.8 (s, 3H), |

TABLE I-continued

| Example | Organohalide | Product: |
|---|---|---|
|  |  | 4.5 (s, 2H), 8.5 (m, 3H); the corresponding hydrochloric acid addition salt had mp 125° C. (dec); NMR (DMSO-d$_6$) δ 2.55 & 2.65 (2s, 3H), 3.7 (s, 3H), 4.5 & 4.6 (2s, 2H), 5.5 (s, 1H), 8.55 (m, 3H), IR (white mineral oil) 2380, 2200, 2120, 1700 cm$^{-1}$; UV λ max (MeOH) 330 nm (ε 12,190), 264 (7,320); Anal Calcd for C$_{11}$H$_{11}$N$_3$O$_2$S$_2$.HCl: C, 41.51% H, 3.81% N, 13.22%; Found: C, 42.14% H, 3.82% N, 13.60%. |
| 5 | 5-(chloromethyl)-pyrimidine | 2-cyano-3-(methylthio)-3-[[(5-pyrimidinyl)-methyl]thio]-2-propenoic acid methyl ester; mp 98–100° C.; NMR (CDCl$_3$) δ 2.5 (s, 3H), 3.8 (s, 3H), 4.35 (s, 2H), 8.7 (s, 2H), 9.1 (s, 1H); IR (CHCl$_3$) 2200, 1705 cm$^{-1}$; UV λ max (MeOH) 331 nm (ε 12,100); Anal Calcd for C$_{11}$H$_{11}$N$_3$O$_2$S$_2$: C, 46.96% H, 3.94% N, 14.93%; Found: C, 46.87% H, 3.89% N, 15.01%. |
| 6 | 2,4-dichloro-pyrimidine-5-carboxylic acid butyl ester | 3-[[2-chloro-5-(butoxycarbonyl)-4-pyrimidin-yl]thio]-2-cyano-3-(methylthio)-2-propenoic acid methyl ester; mp 141–143° C.; NMR (CDCl$_3$) δ 1.0 (t, J = 7Hz, 3H), 1.55 (m, 4H), 2.45 (s, 3H), 3.9 (s, 3H), 4.4 (t, J = 6Hz, 2H), 8.95 (s, 1H); IR (CHCl$_3$) 2215, 1702 cm$^{-1}$; UV λ max (MeOH) 336 nm (ε 13,630), 262 (12,515), 226 (22,225); Anal Calcd for C$_{15}$H$_{16}$ClN$_3$O$_4$S$_2$: C, 44.83% H, 4.01% N, 10.46%; Found: C, 44.74% H, 4.00% N, 10.52%. |
| 7 | 2-(chloromethyl)-thiophene | 2-Cyano-3-(methylthio)-3-[[(2-thienyl)methyl]-thio]-2-propenoic acid methyl ester; mp 64–65° C.; NMR (DMSO-d$_6$) δ 2.6 & 2.73 (2s, 3H), 3.75 (s, 3H), 4.7 (s, 2H), 7.15 (m, 3H); IR (white mineral oil) 2200, 1695 cm$^{-1}$; UV λ max (MeOH) 338 nm (ε 13,040), 232 (10,220); Anal Calcd for C$_{11}$H$_{11}$NO$_2$S$_3$: C, 46.32% H, 3.89% N, 4.90%: Found: C, 46.22% H, 3.87% N, 4.68%. Subsequent disproportionation of this product (cf example 1) gave 2-cyano-3-bis[[2-thienyl)methyl]thio]-2-propenoic acid methyl ester, mp 64–65° C.; NMR (CDCl$_3$) δ 3.82 (s, 3H), 4.45 (s, 2H), 4.6 (s, 2H), 7.05 (m, 6H); IR (CHCl$_3$) 2210, 1710 cm$^{-1}$; UV λ max (MeOH) 334 nm (ε 13,100), 235 (18,700). |
| 8 | 2-(chloromethyl)-3-methylthio-phene | 2-cyano-3-[[(3-methyl-2-thienyl)methyl]-thio]-3-(methylthio)-2-propenoic acid methyl ester; mp 77–79° C.; NMR (benzene-d$_6$, low pulse) δ 1.85 (s, 3H), 2.00 (s, 3H), 4.02 s, 2H), 6.4 & 6.66 (2d, J = 5Hz, 2H); IR (CHCl$_3$) 2210, 1710 cm$^{-1}$; UV λ max (MeOH) 332 nm (ε 12,600), 237 (9,400); Anal Calcd for C$_{12}$H$_{13}$NO$_2$S$_3$: C, 48.13% H, 4.37% N, 4.67%; Found: C, 47.90% H, 4.34% N, 4.57%. |
| 9 | 2-(chloromethyl)-5-methylthiophene | 2-cyano-3-[[(5-methyl-2-thienyl)methyl]thio]-3-(methylthio)-2-propenoic acid methyl ester; mp 66.5–67° C.; NMR (benzene-d$_6$, low pulse) δ 2.0 (s, 6H), 3.3 (s, 3H), 4.05 (s, 2H), 6.25 & 6.45 (2d, J = 3Hz, 2H); IR (CHCl$_3$) 2200, 1695 cm$^{-1}$; UV λ max (MeOH) 332 nm (ε 13,025), 241 (9,170); Anal Calcd for C$_{12}$H$_{13}$NO$_2$S$_3$: C, 48.13% H, 4.37% N, 4.67%; Found: C, 48.22% H, 4.36% N, 4.66%. |
| 10 | 5-chloro-2-(chloromethyl)-thiophene | 2-cyano-3-[[(5-chloro-2-thienyl)methyl]thio]-3-(methylthio)-2-propenoic acid methyl ester; mp 82–83° C.; NMR(benzene-d$_6$) δ 1.95 (s, 3H), 3.25 (s, 3H), 3.72 (s, 2H), 6.2 (m, 2H); IR (CHCl$_3$) 2200, 1700 cm$^{-1}$; UV λ max (MeOH) 333 nm (ε 12,950), 248 (9,720); Anal Calcd for C$_{11}$H$_{10}$ClNO$_2$S$_3$: C, 41.30% H, 3.15% N, 4.38%; Found: C, 41.39% H, 3.16% N, 4.45%. |
| 11 | 3-(chloromethyl)-thiophene | 2-cyano-3-(methylthio)-3-[[(3-thienyl]methyl]-thio]-2-propenoic acid methyl ester; mp 66–67° C.; NMR (benzene-d$_6$, low pulse) δ 1.75 (s, 3H), 32.7 (s, 3H), 3.95 (s, 2H), 6.65 (m, 3H); IR (CHCl$_3$) 2200, 1695 cm$^{-1}$; UV λ max (MeOH) 333 nm (ε 12,760); Anal Calcd for C$_{11}$H$_{11}$NO$_2$S$_3$: C, 46.32% H, 3.89% N, 4.90%; Found: C, 46.26% H, 3.85% N, 4.89%. |

EXAMPLE 12

2-Cyano-3-(methylthio)-3-[[(3-pyridinyl)methyl]thio]-2-propenamide (I; $R^1$=(3-pyridinyl)methylthio, $R^2$=CH$_3$S and $R^3$=HN$_2$)

Potassium carbonate (9.1 g) was added in portions to a stirred solution of 3-(chloromethyl)pyridine hydrochloride (5.42 g) in water (14 mL) and acetonitrile (40 mL). After the evolution of carbon dioxide had ceased, 2-cyano-3-mercapto-3-(methylthio)-2-propenamide (5.2 g), described by R. Gompper and W. Toepfl, Chem. Ber., 95, 2861 (1962), was added to the mixture. The resulting mixture was stirred at 22°–25° C. for 4 hrs, and then at 60° C. for 2 hrs. The solvent of the reaction mixture was removed under reduced pressure. The residue was partitioned between water and ethyl acetate. The ethyl acetate layer was dried (Na$_2$SO$_4$) and filtered through a column of silica gel (120 g). The product was eluted with methanol-ethyl acetate (1:9, v/v) to give 1.3 g of crude product. The crude product was crystallized from ethyl acetate to give the pure title compound; mp 134°–136° C.; NMR (DMSO—d$_6$) δ 2.55 (s, 3H), 4.25 (s, 2H), 7.65 (m, 4H); IR (white mineral oil) 3270, 3150, 2190, 1675 cm$^{-1}$; UV λ max (MeOH) 318 nm (ε 10,750), 271 (5,180), 264 (5,300); Anal. Calcd. for C$_{11}$H$_{11}$N$_3$OS$_2$: C, 49.79% H, 4.18% N, 15.84%; Found: C, 49.90% H, 4.29% N, 15.69%.

EXAMPLE 13

2-Cyano-3-(methylthio)-3-[[(4-pyridinyl)methyl]thio]-2-propenamide (I: $R^1$=(4-pyridinyl)methylthio, $R^2$=CH$_3$S and $R^3$=NH$_2$)

Potassium carbonate (40.95 g) was added gradually to a stirred suspension of 4-(chloromethyl)pyridine hydrochloride (24.42 g) in acetonitrile (270 mL) and water (90 mL). The mixture was stirred for 10 min. Thereafter, 2-cyano-3-mercapto-3-(methylthio)-2-propenamide (23.55 g) was added to the mixture, and the resulting mixture was stirred at 20° to 22° C. for 24 hrs. The solvent was evaporated from the reaction mixture. The residue was diluted with water and the resulting mixture was shaken with ethyl acetate. Insoluble material was collected by filtration and washed with cold methanol. The solid (13.1 g) was recrystallized from a large volume of methanol to give the title compound (4.5 g); mp 144°–146° C.: NMR (DMSO—d$_6$) δ 2.45 (s, 3H), 4.25 (s, 2H), 7.3 & 8.5 (d, 4H), 7.65 (broad, 2H); IR (white mineral oil) 3260, 3130, 2200, 1685 cm$^{-1}$; UV λ max (MeOH) 320 nm (ε 10,265); Anal. Calcd. for C$_{11}$H$_{11}$N$_3$OS$_2$: C, 49.79% H, 4.18% N, 15.84%; Found: C, 49.54% H, 4.07% N, 15.68%.

We claim:

1. A compound of formula I

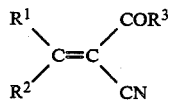

(I)

wherein $R^1$ is S(CH$_2$)$_m$—Het in which m is an integer from zero to three and Het is an unsubstituted or monosubstituted heterocyclic selected from the group consisting of pyridinyl, (N-oxide)pyridinyl, the substituent being selected from lower alkyl, lower alkoxy, halo, trifluoromethyl or (CH$_2$)$_n$COOQ wherein n is an integer from 0 to 2 and Q is lower alkyl; $R^2$ is lower alkylthio, lower alkenylthio or S(CH$_2$)$_m$—Het wherein m and Het are as defined herein; and $R^3$ is lower alkoxy or amino.

2. The compound of claim 1 wherein $R^1$ is S(CH$_2$)$_m$—Het wherein m is the integer zero or one and Het is as defined in claim 1, and $R^2$ is lower alkylthio, or the same S(CH$_2$)$_m$—Het radical as selected for $R^1$.

3. The compound of claim 1 wherein $R^1$ is S(CH$_2$)$_m$—Het wherein m is the integer zero or one and Het is pyridinyl, (N-oxide)pyridinyl and $R_2$ is lower alkylthio.

4. A therapeutically acceptable acid addition salt of the compound of claim 1 provided that it contains a basic nitrogen.

5. The compound of claim 1 which is 2-cyano-3-(methylthio)-3-[[(3-pyridinyl)methyl]thio]-2-propenoic acid methyl ester.

6. The compound of claim 1 which is 2-cyano-3,3-bis[[(3-pyridinyl)methyl]thio]-2-propenoic acid methyl ester.

7. The compound of claim 1 which is 2-cyano-3-(methylthio)-3-[[(3-pyridinyl)methyl]thio]-2-propenoic acid methyl ester N-oxide.

8. The compound of claim 1 which is 2-cyano-3-(methylthio)-3-[[(3-pyridinyl)methyl]thio]-2-propenamide.

9. The compound of claim 1 which is 2-cyano-3-(methylthio)-3-[[(4-pyridinyl)methyl]thio]-2-propenamide.

10. A method for preventing or treating gastrointestinal ulcers in a mammal, which comprises administering to the mammal in need thereof an effective amount of the compound of claim 1, or a therapeutically acceptable acid addition salt of the compound provided that it has a basic nitrogen.

11. A method for preventing or decreasing the secretion or availability of excessive amounts of gastric acid in a mammal suffering from hyperchlorhydria, which comprises administering to the mammal in need thereof an effective amount of the compound of claim 1, or a therapeutically acceptable acid addition salt of the compound provided that it has a basic nitrogen.

12. A pharmaceutical composition in unit dosage form for preventing or treating gastrointestinal ulcers in a mammal, which comprises an effective amount of a compound of claim 1, or a therapeutically acceptable acid addition salt of the compound provided that it has a basic nitrogen, and a pharmaceutically acceptable carrier.

13. A pharmaceutical composition in dosage unit form for suppressing gastric acid secretions in a mammal, which comprises an effective amount of a compound of claim 1, or a therapeutically acceptable acid addition salt of the compound provided that it has a basic nitrogen atom, and a pharmaceutically acceptable carrier.

* * * * *